US011015186B2

(12) United States Patent
Mak et al.

(10) Patent No.: US 11,015,186 B2
(45) Date of Patent: May 25, 2021

(54) MAXIMIZING DNA YIELD OF BLOOD SPECIMENS COLLECTED IN RAPID CLOT TUBES

(71) Applicant: Abbott Molecular Inc., Des Plaines, IL (US)

(72) Inventors: Wai-Bing Mak, Des Plaines, IL (US); Dominik Duelli, Des Plaines, IL (US); Shihai Huang, Des Plaines, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 489 days.

(21) Appl. No.: 15/698,326

(22) Filed: Sep. 7, 2017

(65) Prior Publication Data

US 2018/0087049 A1 Mar. 29, 2018

Related U.S. Application Data

(60) Provisional application No. 62/400,488, filed on Sep. 27, 2016.

(51) Int. Cl.
*C12Q 1/68* (2018.01)
*C12N 15/10* (2006.01)
*C12Q 1/6806* (2018.01)
*C12Q 1/70* (2006.01)

(52) U.S. Cl.
CPC ..... *C12N 15/1006* (2013.01); *C12N 15/1013* (2013.01); *C12Q 1/6806* (2013.01); *C12Q 1/706* (2013.01)

(58) Field of Classification Search
None
See application file for complete search history.

(56) References Cited

U.S. PATENT DOCUMENTS

| | | | |
|---|---|---|---|
| 3,920,549 A | 11/1975 | Gigliello et al. | |
| 5,075,430 A | 12/1991 | Little | |
| 5,342,931 A | 8/1994 | Woodward et al. | |
| 5,658,548 A | 8/1997 | Padhye et al. | |
| 6,686,204 B2 | 2/2004 | Dubrowny et al. | |
| 6,855,499 B1 | 2/2005 | Nargessi | |
| 6,869,532 B2 | 3/2005 | Arnold et al. | |
| 10,287,570 B2 * | 5/2019 | Qian | B01L 3/502 |
| 2011/0092687 A1 * | 4/2011 | Bendzko | C12N 9/2462 536/23.1 |
| 2014/0272967 A1 | 9/2014 | Gundling | |

FOREIGN PATENT DOCUMENTS

| | | | | |
|---|---|---|---|---|
| WO | WO-2014029791 A1 * | 2/2014 | ........... | C12Q 1/6806 |
| WO | WO 2016/147004 A1 | 9/2016 | | |

OTHER PUBLICATIONS

Terry et al. (Encyclopedia of Medical Devices and Instrumentation, Second Edition, edited by John Webster, 2006, p. 455-465) (Year: 2006).*
Regan et al. (J of Molecular Diagnostics, 2012, 14(2):120-129) (Year: 2012).*
Javadi et al. (Tanaffos, 2014, 13(4):41-47) (Year: 2014).*
Berensmeier, "Magnetic particles for the separation and purification of nucleic acids." Appl Microbiol Biotechnol. Dec. 2006; 73(3):495-504.
Bergallo, et al., "Evaluation of six methods of viral DNA from urine and serum samples." New Microbiologica, 2006, 29(2): 111-119.
Bienvenue, et al., DNA Extraction on Microfluidic Devices. Forensic Sci Rev, 2010. 22(2): p. 187-97.
Bowen, et al., "Interferences from blood collection tube components on clinical chemistry assays." Biochem Med (Zagreb). Feb. 15, 2014; 24(1):31-44.
Budak, et al., "Evaluation in an emergency department of rapid separator tubes containing thrombin for serum preparation prior to hs-cTnT and CK-MB analyses." BMC Clin Pathol, 2013. 13: p. 20.
Chacon-Cortes & Griffiths, "Methods for extracting genomic DNA from whole blood samples: current perspectives" Journal of Biorepository Science for Applied Medicine, 2: 1-9 (2014).
Changotra, et al., "An improved method for the isolation of hepatitis B virus DNA from human serum." Indian J Virol. Sep. 2013; 24(2):174-9.
Esser, et al., "Nucleic acid-free matrix: Regeneration of DNA binding columns." BioTechniques 2005, 39(2): 270-271.
Ghatak, et al., "A simple method of genomic DNA extraction from human samples for PCR-RFLP analysis." J Biomol Tech. Dec. 2013; 24(4):224-31.
Gjerde, et al., RNA Purification and Analysis: Sample Preparation, Extraction, Chromatography, First Edition, Wiley-VCH, Weinheim, Germany (2009).
Henry's Clinical Diagnosis and Management by Laboratory Methods, vol. 1, W.B Saunders Company, Philadelphia, PA, p. 60 (1979).
Klop, et al., "Dyslipidemia in obesity: mechanisms and potential targets." Nutrients, 2013. 5(4):1218-40.
Lu, et al., "Rapid quantification of hepatitis B virus DNA by real-time PCR using efficient TaqMan probe and extraction of virus DNA." World J Gastroenterol. Dec. 7, 2006;12(45):7365-70.
McEnroe, Burritt, Powers, CLSI, Interference Testing in Clinical Chemistry; Approved Guideline—Second Edition. EP7-A2, 2008. 25(27): p. 77.
Ng & Yeo, "Thrombin-accelerated quick clotting serum tubes: an evaluation with 22 common biochemical analytes." Adv Hematol, 2013. 2013: p. 769479.
Sambrook, et al., Molecular Cloning: A Laboratory Manual, 4th ed., Cold Spring Harbor Press, Cold Spring Harbor, New York (2012); Preface and Table of Contents Only.
Seftel, et al., "The prevalence of hypertension, hyperlipidemia, diabetes mellitus and depression in men with erectile dysfunction." J Urol, 2004. 171(6 Pt 1): p. 2341-5.

(Continued)

*Primary Examiner* — Stephanie K Mummert
(74) *Attorney, Agent, or Firm* — Casimir Jones, S.C.; Melissa Karabinis

(57) ABSTRACT

The invention provides methods for isolating DNA from a blood sample collected into tubes containing a rapid clot activator, which involves the use of a lysis buffer comprising an alcohol.

19 Claims, 4 Drawing Sheets

(56) References Cited

OTHER PUBLICATIONS

Sidim & Acar, "Alcohols Effect on Critic Micelle Concentration of Polysorbate 20 and Cetyl Trimethyl Ammonium Bromine Mixed Solutions." J Surfactants Deterg, 2013. 16(4): p. 601-607.

Steindel & Howanitz, "Physician satisfaction and emergency department laboratory test turnaround time." Arch Pathol Lab Med. Jul. 2001; 125(7):863-71.

Strathmann, et al., "Use of the BD vacutainer rapid serum tube reduces false-positive results for selected beckman coulter Unicel Dxl immunoassays." Am J Clin Pathol, 2011. 136(2): p. 325-9.

Sun, et al., "Optimization of influencing factors of nucleic acid adsorption onto silica-coated magnetic particles: application to viral nucleic acid extraction from serum." J Chromatogr A, 2014. 1325: p. 31-9.

Tan & Yiap, "Review Article DNA, RNA, and Protein Extraction: The Past and The Present" Journal of Biomedicine and Biotechnology, vol. 2009, Article ID 574398, 10 pages.

Thavasu, et al., "Measuring cytokine levels in blood. Importance of anticoagulants, processing, and storage conditions." J Immunol Methods. Aug. 30, 1992; 153 (1-2):115-24.

* cited by examiner

US 11,015,186 B2

MAXIMIZING DNA YIELD OF BLOOD SPECIMENS COLLECTED IN RAPID CLOT TUBES

CROSS-REFERENCE TO RELATED APPLICATION(S)

This patent application claims the benefit of U.S. Provisional Patent Application No. 62/400,488, filed Sep. 27, 2016, which is incorporated by reference herein.

TECHNICAL FIELD

This disclosure relates to methods and compositions for isolating DNA from blood specimens collected using rapid clot tubes.

BACKGROUND

In blood collection, the use of rapid clot sample tubes is becoming more prevalent, especially in Asia-Pacific countries. Rapid clot tubes reduce the work load and time required for sample preparation prior to analysis, which can help patient throughput, especially in emergency rooms, where decisions to management are often based on blood tests (Steindel S. and Howanitz P., *Arch Pathol Lab Med*, 125: 863-71 (2001). In diagnostic applications, such as immunoassays, rapid clot tubes are preferred because they reduce false-positive results, and have been shown to reduce hemolysis, which can interfere with sownstream analyses. Rapid clot tubes sometimes also contain a gel that separates blood cells from serum (i.e., serum separator gel). Such "serum separator tubes" or "SST" require short processing times, yield higher serum levels, limit hazardous aerosolization, and allow for shipping and freezing of blood, thereby improving the convenience of phlebotomy and preventing contamination of the serum post-collection (see, e.g., Bowen, R. A. R. and Remaley, A. T., *Biochemia Medica*, 24(1): 31-44 (2014)).

Despite the advantages of rapid clot tubes and serum separator tubes, studies have revealed that components of such collection tubes can leach into specimens and adsorb analytes (such as DNA) from a specimen, which can cause pre-analytical error in laboratory testing and/or false negative results. As such, these increasingly popular blood collection tubes may be incompatible with certain analytes (e.g., nucleic acids) used for molecular diagnostic tests.

Therefore, there is a need for improved methods of isolating DNA from blood samples collected using rapid clot tubes that is compatible with molecular diagnostic tests.

SUMMARY

The present disclosure provides a method for isolating deoxyribonucleic acid (DNA) in a blood sample, the method comprising (a) collecting a blood sample from a subject into tubes comprising a rapid clot activator, wherein the blood sample comprises cells, a virus, and/or bacteria; (b) contacting the blood sample with a lysis buffer comprising an alcohol, wherein the lysis buffer lyses the cells, virus, and/or bacteria to release DNA from the cells, virus, and/or bacteria; (c) contacting the lysed cells, virus, and/or bacteria with a solid support which binds to the DNA; (d) washing the solid support bound to the DNA with a wash buffer; and (e) eluting the DNA from the solid support with an elution buffer, thereby isolating the DNA.

In one aspect of the above method, the tubes further comprise a serum separator gel.

In another aspect of the above method, the lysis buffer comprises between about 20% to about 70% alcohol.

In another aspect of the above method, the lysis buffer comprises between about 33% to about 65% alcohol.

In a further aspect of the above method, the lysis buffer comprises about 50% alcohol.

In another aspect, the alcohol is ethanol, methanol, propanol, or combinations thereof.

In yet another aspect, the method comprises contacting the blood sample with proteinase K before step (b).

In another aspect, the method comprises contacting the blood sample with proteinase K after step (b).

In a further aspect of the above method, the rapid clot activator comprises silica microparticles.

In another aspect, the rapid clot activator comprises thrombin.

In another aspect, the solid support comprises magnetic microparticles.

In yet another aspect of the above method, the wash buffer comprises Tris, guanidinium thiocyanate (GITC), and Tween.

In another aspect, the above method comprises an additional washing step with a second wash buffer before step (e).

In another aspect, the second wash buffer comprises water.

In another aspect, the elution buffer comprises water.

In another aspect of the above method, the DNA is genomic DNA.

In yet another aspect, the DNA is used as a template in a PCR reaction.

In a further aspect, the blood sample comprises cells.

In another aspect, the cells are animal cells.

In another aspect, the cells are human cells.

In further aspect of the above method, the blood sample comprises a virus.

In yet another aspect, the blood sample comprises bacteria.

In yet another aspect, the blood sample comprises protozoans, helminths, or fungi.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1:
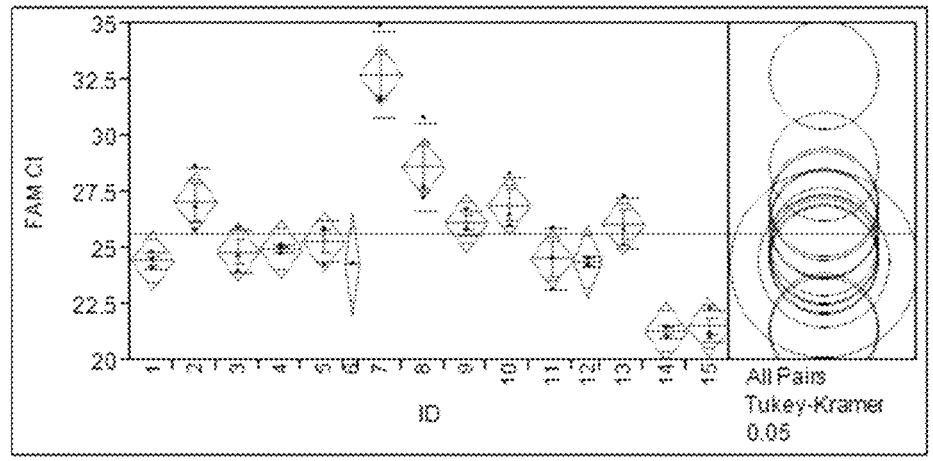
FIG. 1 is a graph illustrating the reduction in Hepatitis B virus DNA yield isolated from blood collected in standard and rapid clot tubes.

Embodiments of the present disclosure relate to methods and compositions for isolating DNA from blood samples using rapid clot tubes. The present disclosure is based, at least in part, on the discovery that inaccurate quantification of analytes from blood samples collected in rapid clot tubes (RCT) or serum separator tubes (SST) appears to be caused by carryover components of the tube (e.g., silica microbeads in a rapid clotting tube), which can remain in the serum after centrifugation. These carryover components may compete with microparticles for binding of target DNA during DNA isolation procedures. DNA bound to the tube components may be washed away and discarded if the tube components do not associate with the microparticles, resulting in failure to capture the DNA for subsequent processing steps.

1. Definitions

Before the embodiments of the present disclosure are described, it is to be understood that this invention is not limited to particular embodiments described, and as such may vary. It is also to be understood that the terminology used herein is for the purpose of describing particular embodiments only, and is not intended to be limiting.

"Component," "components," or "at least one component," refer generally to a calibrator, a control, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum, whole blood, tissue aspirate, or plasma sample, in accordance with the methods described herein and other methods known in the art. Some components can be in solution or lyophilized for reconstitution for use in an assay. A component also may be an element or constituent of a blood collection tube.

"Contacting," and grammatical equivalents thereof, refers to any type of combining action which brings one component or element into sufficiently close proximity with another component or element such that some type of interaction occurs between the two components or elements (e.g., a binding interaction). Contacting may be achieved in a variety of different ways, including combining two or more components or elements, exposing one component or element to a second component or element by introducing the first component or element in close proximity to the second component or element, and the like.

"Control" as used herein refers to a reference standard for an analyte such as is known or accepted in the art, or determined empirically using acceptable means such as are commonly employed. A "reference standard" is a standardized substance which is used as a measurement base for a similar substance. For example, there are documented reference standards published in the U.S. Pharmacopeial Convention (USP-NF), Food Chemicals Codex, and Dietary Supplements Compendium (all of which are available at usp.org), and other well-known sources. Methods for standardizing references are described in the literature. Also well-known are means for quantifying the amounts of analyte present by use of a calibration curve for analyte or by comparison to an alternate reference standard. Alternate reference standards that have been described in the literature include standard addition (also known as the method of standard addition), or digital polymerase chain reaction.

The term "isolating," as used herein, refers to removing a material from its natural environment. For example, DNA may be isolated from a cell, sample of cells, microorganisms (e.g., bacteria), or viruses.

As used herein, the terms "nucleic acid," "nucleic acid sequence," "oligonucleotide," and "polynucleotide" refer to at least two nucleotides covalently linked together. The depiction of a single strand also defines the sequence of a complementary strand. Thus, a nucleic acid sequence also encompasses the complementary strand of a depicted single strand. Nucleic acid sequences can be single-stranded or double-stranded, or can contain portions of both double-stranded and single-stranded sequences. The nucleic acid can be DNA, both genomic and complimentary DNA (cDNA), RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods. A particular nucleic acid sequence can encompass conservatively modified variants thereof (e.g., codon substitutions), alleles, orthologs, single nucleotide polymorphisms (SNPs), and complementary sequences as well as the sequence explicitly indicated.

A "rapid clot activator" is a substance that induces the formation of a blood clot within about 5 minutes to about 20 minutes of contact with a blood sample (Steindel and Howantiz, supra). A rapid clot activator may use intrinsic or extrinsic pathways of clot formation. Whole blood contains all of the necessary factors to inducing clotting by the intrinsic pathway. Clot activation by the intrinsic pathway is surface area dependent, and a greater density of activating surface sites speeds clotting time. Greater surface area may be provided by particular activators, such as, for example, siliceous substances (e.g., glass, silica, kaolin, bentonite, diatomaceious earth) (see, e.g., Bowen and Remaley, supra, and U.S. Pat. No. 6,686,204). In the extrinsic clotting pathway, coagulation of blood is induced by adding substances to a blood sample that are extrinsic to blood, such as, for example, ellagic acid, thrombin, snake venoms, and thromboplastin (see, e.g., Bowen and Remaley, supra, and U.S. Pat. No. 6,686,204).

A "serum separator gel" refers to a thixotropic gel that has a specific gravity that falls between the specific gravity of the serum and the cellular phases of a blood sample. Suitable thixotropic gels that may be used in the method described herein include polymers comprising alkyl acrylates and/or alkyl methacrylates. However, any suitable gel-like composition which can be used as a barrier between blood portions separated in a centrifuge may be used.

As used herein, the term "solid support" means any solid surface to which an analyte or analyte-binding molecule (e.g., a nucleic acid or an antibody) can be attached such that the analyte or analyte-binding molecule cannot break free from the solid support in a liquid medium. A solid support can easily be separated from a liquid which the solid support contacts. Examples of solid supports include, but are not limited to, a particle, a microparticle, a bead (e.g., latex, agarose, sepharose, streptavidin, tosylactivated, epoxy, polystyrene, amino bead, amine bead, carboxyl bead), an electrode, a multiwell plate, and a slide. The solid support can be comprised of any suitable material, such as, for example, ceramic, glass, polymers (e.g., cellulose, sepharose), metals, or silica.

The terms "tube," "blood collection tube," "BCT," or "collection tube" are synonymous and refer to glass or plastic tubes used to collect blood that comprise tube walls and rubber stoppers, and may contain one or all of the following: lubricants, anticoagulants, separator gels, clot activators, and surfactants. The blood collection tube can be a serum collection tube, which typically contains a clot activator (e.g., silica particles or thrombin) and/or a serum separator gel, both of which are defined above. Alternatively, the blood collection tube can be a plasma collection tube. Plasma collection tubes typically contain an anti-coagulant (e.g., EDTA) and thus also are referred to as "anti-coagulation tubes." Rubber stoppers of blood collection tubes are routinely color-coded according to the tube type and presence of serum separator gel, and generally depend on the tube manufacturer. Blood collection tubes are further described in, e.g., Henry, J. B., *Clinical Diagnosis and Management by Laboratory Methods*, Volume 1, W. B Saunders Company, Philadelphia, Pa., p. 60 (1979); Thavasu, P. W., et al., *J Immunol Methods*, 153: 115-124 (1992); and Bowen and Remaley, supra).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. The materials, methods, and examples disclosed herein are illustrative only and not intended to be limiting.

2. Methods for Isolating DNA

Described herein are methods for isolating DNA from cells, viruses, and/or bacteria in a blood sample. In certain embodiments, the method for isolating DNA may involve determining the presence of and/or concentration of a DNA of interest in a sample. In other embodiments, the method may also be used for determining presence of and/or concentration of a plurality of different DNA molecules of interest in a sample.

In one aspect, the method comprises collecting a blood sample from a subject into tubes comprising a rapid clot activator; contacting the blood sample with a lysis buffer which comprises an alcohol, wherein the lysis buffer lyses the cells, viruses, or bacteria to release DNA from the cells, viruses, or bacteria in the blood; contacting the lysed cells, viruses, or bacteria with a solid support that binds to the DNA; washing the solid support bound to the DNA with a wash buffer; and eluting the DNA from the solid support with an elution buffer.

The general steps of nucleic acid purification include cell, virus, or bacteria lysis, which disrupts the cellular, viral, or bacterial structure to create a lysate, inactivation of cellular nucleases such as DNase and RNase, inactivation of proteases, and separation of the desired nucleic acid from cell debris. These steps as they relate to the present disclosure are described in detail below. DNA isolation methods also are described in, for example, Tan, S. C., and Yiap, B. C., *Journal of Biomedicine and Biotechnology*, Volume 2009, Article ID 574398 (2009), Ghatak et al., *Journal of Biomolecular Techniques*, 24(4): 224-231 (2013), Ausubel et al., *Current Protocols in Molecular Biology*, John Wiley & Sons, New York (2016); and Chacon-Cortes, D., and Griffiths, L. R., *Journal of Biorepository Science for Applied Medicine*, 2: 1-9 (2014).

a) Sample

As used herein, the terms "blood sample", "sample", "test sample", "biological sample" refer to a blood sample containing or suspected of containing an analyte of interest (e.g., DNA). The blood sample may be derived from any suitable source. The sample may be used immediately after collection or may be stored prior to use. Methods well-known in the art for collecting, handling, processing, and storing blood samples are used in the practice of the present disclosure.

Any suitable volume of blood sample may be used in the methods described herein. A wide range of volumes of the blood sample may be analyzed, including, for example, about 0.5 nL, about 1 nL, about 3 nL, about 0.01 μL, about 0.1 μL, about 1 μL, about 5 μL, about 10 μL, about 100 μL, about 1 mL, about 5 mL, about 10 mL, or a range defined by any of the foregoing values. In some embodiments, the volume of the blood sample is between about 0.01 μL and about 10 mL, between about 0.01 μL and about 1 mL, between about 0.01 μL and about 100 μL, or between about 0.1 μL and about 10 μL, or a range defined by any of the foregoing values.

In some embodiments, the blood sample may be diluted prior to DNA isolation. For example, in embodiments where the source the sample is a human, the blood sample may be diluted with an appropriate solvent (e.g., a buffer such as PBS buffer). A blood sample may be diluted about 1-fold, about 2-fold, about 3-fold, about 4-fold, about 5-fold, about 6-fold, about 10-fold, about 100-fold, or greater, prior to use.

In some embodiments, the blood sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the blood sample may be concentrated prior to use in an assay. For example, in embodiments where the source of the sample is a human, the blood sample may be concentrated by precipitation, evaporation, filtration, centrifugation, or a combination thereof. A blood sample may be concentrated about 1-fold, about 2-fold, about 3-fold, about 4-fold, about 5-fold, about 6-fold, about 10-fold, about 100-fold, or greater, prior to use.

As used herein, the terms "subject" and "patient" are used interchangeably. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc.) and a human). Preferably, the subject is a human.

In addition to comprising blood cells, in certain embodiments, the blood sample may also comprise infectious agents present in an animal's bloodstream (e.g., viruses, bacteria, and/or parasites). Thus, the DNA isolated by the method described herein may be cellular DNA or DNA frome one or more infectious agents. Infectious agents include, for example, bacteria, viruses, fungi, and parasites. In some embodiments, the DNA isolated from a blood sample may be from any of the following bacteria: *Actinomyces, Anabaena, Bacillus, Bacteroides, Bdellovibrio, Caulobacter, Chlamydia, Chlorobium, Chromatium, Clostridium, Cytophaga, Deinococcus, Escherichia, Halobacterium, Heliobacter, Hyphomicrobium, Methanobacterium, Micrococcus, Myobacterium, Mycoplasma, Myxococ-* cus, *Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema.*

In other embodiments, the DNA isolated from a blood sample may be from any of the following viruses: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae (e.g., Hepatitis B virus), Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenza virus A and B), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxyiridae (e.g., vaccinia virus), Reoviridae (e.g., rotavirus), Retroviridae (e.g., lentivirus, such as human immunodeficiency virus (HIV) 1 and HIV 2), Rhabdoviridae, Totiviridae, Crimean-Congo haemorrhagic fever virus, Eastern Equine Encephalitis virus, Hendra virus, Lassa fever virus, Monkeypox virus, Nipah virus, Rift Valley fever virus, South American Haemorrhagic Fever viruses, Venezuelan Equine Encephalitis virus, and Zika virus.

In other embodiments, the DNA isolated from a blood sample may be from any of the following parasites: *Sporozoa* (e.g., *Plasmodium* species), *Ciliophora, Rhizopoda,* or *Zoomastigophora*; helmiths (Nematoda, Cestoda, Trematoda), and protozoans (Trypanosomes, Leismania, Etamoeba, Giardia, Trichomonas, and Balantidium).

b) Rapid Clot Tubes

In some embodiments, the methods disclosed herein involve collecting a blood sample from a subject into tubes comprising a rapid clot activator. Such tubes typically are serum collection tubes (described above) and are often referred to in the art as "rapid clot tubes," "rapid serum tubes," or "RST." As discussed above, suitable rapid clot activators that can be used in the methods disclosed herein include, for example, silicious substances (e.g., glass, silica, kaolin, bentonite, diatomaceious earth), which activate clot formation through the intrinsic pathway, and ellagic acid, thrombin, snake venoms, and thromboplastin, which activate clotting through the extrinsic pathway (see, e.g., Bowen and Remaley, supra, and U.S. Pat. No. 6,686,204). In certain embodiments, the clot activator used in the methods disclosed herein may be silica microparticles, Z-clot activator (microscopic silica beads), Greiner Bio-One GmbH, Kremsmünster, Austria) or thrombin. Other rapid clot activators that can be used in methods described herein are commercially available from a variety of sources, including, for example Sarstedt AG & Co. (Nümbrecht, Germany).

In some embodiments, the rapid clot tubes may also comprise a serum separator gel. As discussed above, a serum separator gel is used to separate serum from clotted whole blood or plasma from cells (see, e.g., U.S. Pat. No. 3,920, 549). Collection tubes containing serum separator gels are often referred to in the art as "serum separator tubes" or "SST." The serum separator gel may be a thixotropic gel that has a specific gravity that falls between the specific gravity of the serum and the cellular phases of a blood sample. Suitable thixotropic gels may include a polymer comprising alkyl acrylates and/or alkyl methacrylates. However, any suitable gel-like composition which can be used as a barrier between blood portions separated in a centrifuge may be used.

A variety of commercially available rapid clot tubes (with and without serum separator gel) can be used in the methods described herein. Such rapid clot tubes include, but are not limited to, VACUETTE® Z Serum Clot Activator Tubes ("Z-clot") (Greiner Bio-One GmbH, Kremsmünster, Austria), VACUTAINER® Rapid Serum Tubes (RST), SST II Advance Tubes, and SST Plus Tubes (all from BD Biosciences, San Jose, Calif.). Rapid clot tubes (with and without serum separator gels) available from other commercial sources, such as Sekisui Diagnostics GmbH (Pfungstadt, Germany), Terumo BCT (Lakewood, Colo.), Nipro Medical Corporation (Bridgewater, N.J.), and Fisher Scientific (Waltham, Mass.) also may be used.

c) Sample Digestion and Lysis

Following collection of the blood sample into rapid clot tubes, the method disclosed herein further comprises contacting the blood sample with a lysis buffer, which lyses the cells, virus, and/or bacteria to release DNA from the cells, virus, and/or bacteria. The term "lysis," as used herein, refers to the dissolution or destruction of cells, viruses, and/or bacteria as a result of the disruption of the cell or viral membrane or viral coat. A "lysis buffer" is a solution used to lyse cells, virus, and/or bacteria, which typically comprises one or more detergents and salts. Examples of suitable salts that can be included in the lysis buffer include tris (hydroxymethyl)aminomethane (Tris), Tris-HCl, EDTA, and NaCl, which regulate the acidity or osmolarity of the lysate. Examples of suitable detergents that can be included in the lysis buffer include sodium deoxycholate, sodium dodecylsulfate (SDS), Triton X-100, TWEEN, guanidinium thiocyanate (GITC) and NP-40. In one embodiment, the lysis buffer further comprises an alcohol. Lysis buffer can be prepared using routine methods in the art, such as those described in, e.g., Sambrook et al., *Molecular Cloning: A Laboratory Manual,* 4th ed., Cold Spring Harbor Press, Cold Spring Harbor, N.Y. (2012); and Ausubel et al., *Current Protocols in Molecular Biology,* John Wiley & Sons, New York (2016), or obtained from commercial sources.

In some embodiments, the method described herein further comprises removing or inactivating protein contaminants, such as nucleases (e.g., DNase), which may otherwise degrade or contaminate the DNA of interest in the sample. Thus, the method may further comprise treating the lysed cells, viruses, and/or bacteria with a protease before, after, or concurrently with the lysis buffer. Any protease that can be used to remove or inactive protein contaminants in DNA isolation methods can be used, such as, for example proteinase K. Proteinase K is a broad spectrum serine protease that is widely used for digestion of proteins in nucleic acid extraction protocols. Proteinase K cleaves peptide bonds at the carboxylic side chains of aliphatic, aromatic, or hydrophobic amino acids. Any suitable proteinase K can be used in the methods described herein, such as those commercially available from sources such as, e.g., Sigma Aldrich (St. Louis, Mo.), Thermo Fisher Scientific (Waltham, Mass.), and New England Biolabs (Ipswich, Mass.).

In some embodiments, the blood sample may be contacted with proteinase K prior to contacting the blood sample with lysis buffer. In other embodiments, the blood sample may be treated with proteinase K after the blood sample is contacted with lysis buffer. In other embodiments, the lysis buffer may be partially or completely mixed with proteinase K and added to the sample simultaneously.

i. Alcohol in Lysis Buffer

In one embodiment, the lysis buffer may comprise an alcohol, which has been shown to improve DNA recovery from blood samples collected into rapid clot tubes. The lysis buffer may comprise any suitable alcohol that improves yield of DNA recovery from blood samples. Suitable alcohols include, but are not limited to, ethanol, methanol, propanol, and the like, or combinations thereof.

The lysis buffer may comprise any suitable amount of alcohol, so long as the alcohol does not associate with lipids naturally present in the blood to form adducts (which may interfere with sample preparation and/or DNA extraction). In some embodiments, the lysis buffer may comprise between about 20% to about 70% alcohol (e.g., about 20%, about 25%, about 30%, about 35%, about 40%, about 45%, about 50%, about 55%, about 60%, about 65%, about 70%, or a range defined by any two of the foregoing values). In other embodiments, the lysis buffer may comprise between about 33% and about 65% alcohol (e.g., about 33%, about 38%, about 43%, about 48%, about 53%, about 58%, about 65%, or a range defined by any two of the foregoing values). In another embodiment, the lysis buffer may comprise between about 40% and about 50% alcohol (e.g., about 41%, about 42%, about 43%, about 44%, about 45%, about 46%, about 47%, about 48%, about 49%, about 50%, or a range defined by any two of the foregoing values). It is believed that alcohol concentrations of 65% or higher may lead to aggregation of magnetic particles, if used to extract DNA, resulting in loss of detectable DNA in the eluate.

d) Solid Support

Following lysis of the cells, viruses, and/or bacteria in the blood sample to release DNA from the cells, viruses, and/or bacteria, the method described herein comprises contacting the lysed cells, viruses, and/or bacteria with a solid support which binds to the DNA. DNA purification that utilizes a solid support is often referred to in the art as "solid-phase" nucleic acid extraction. In some embodiments, the solid support comprises silica. A solid support can easily be separated from a liquid which the solid support contacts. Systems for solid-phase purification typically will absorb nucleic acid in the extraction process depending on the pH and salt content of the buffer used. Adsorption of nucleic acid to the solid support can occur via any suitable interaction between the target nucleic acid and the solid support, including, for example, hydrogen-binding interaction with a hydrophilic matrix under chaotropic conditions, ionic exchange under aqueous conditions by means of an anion exchanger, and affinity and size exclusion mechanisms.

Solid-phase purification may be performed by using a spin column, operated under centrifugal force. Any suitable solid support can be used to purify the DNA from the blood samples. Suitable solid supports include, but are not limited to, silica matrices, glass particles, diatomaceous earth, and anion-exchange carriers. Examples of silica matrices that may be used as the solid support include, but are not limited to, glass particles, such as glass powder, silica particles, and glass microfibers prepared by grinding glass fiber filter papers, and including diatomaceous earth. In other embodiments, the solid support may be a magnetic particle, such as a bead or microparticle. Magnetic separation is widely used in solid-phase nucleic acid purification methods, and several magnetic carriers are commercially available.

In some embodiments, the solid support is a magnetic or paramagnetic bead. In certain embodiments, the bead may be a particle, e.g., a microparticle. It will be appreciated that the size of microparticle can vary depending on the application. In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and 700 nm, or between about 500 nm and 700 nm. For example, the microparticle may be about 4-6 microns, about 2-3 microns, or about 0.5-1.5 microns. Particles less than about 500 nm are sometimes considered nanoparticles. Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

Magnetic beads/particles/microparticles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include $NiFe_2O_4$, $CoFe_2O_4$, $Fe_3O_4$ (or $FeO.Fe_2O_3$). Beads, particles, or microparticles can have a solid core portion that is magnetic and is surrounded by one or more non-magnetic layers. Alternatively, the magnetic portion can be a layer around a non-magnetic core. The solid support may be in stored in dry form or in a liquid.

Solid-phase nucleic acid extraction methods are further described in, e.g., Esser et al., *BioTechniques*, 39(2): 270-271, 2005; Gjerse et al., *RNA Purification and Analysis: Sample Preparation, Extraction, Chromatography*, First Edition, Wiley-VCH, Weinheim, Germany (2009); Berensmeier, S., *Applied Microbiology and Biotechnology*, 73(3): 495-504, (2006); and U.S. Pat. Nos. 5,075,430, 5,342,931, 5,658,548, 6,855,499, and 6,869,532.

e) DNA Washing and Elution

In certain embodiments, the method described herein may include washing the solid support one or more times in order to remove unwanted components of the lysed cells, virus, and/or bacteria or other debris, leaving only the DNA bound to the solid support. The one or more washing steps can be performed using any suitable wash buffer, several of which are well known in the art. In some embodiments, the wash buffer comprises one or more detergents and salts, such as those described above with respect to lysis buffer. For example, a wash buffer may comprise Tris, GTIC, and/or Tween. In another embodiment, a wash buffer may comprise water.

In accordance with the method described herein, the solid support is washed at least once with a wash buffer prior to eluting the DNA from the solid support. In some embodiments, however, the solid support is washed at least twice (e.g., 2, 3, 4, 5, or more times) prior to eluting the DNA from the solid support, in which case the wash buffer may be the same for each wash step, or different wash buffers may be used for each wash step. In one embodiment, for example, a first washing step may involve a first wash buffer comprising Tris, GTIC, and Tween, and a second washing step may involve a second wash buffer comprising water. Other subsequent (third, fourth, fifth, etc.) washing steps may be performed in order to effectively remove cellular, viral, and/or bacterial debris from the solid support.

Following washing, the method described herein comprises eluting the DNA from the solid support with an elution buffer, thereby isolating the DNA. An "elution buffer" is a solution used to remove the nucleic acid from the solid support. For DNA extraction methods, a typical elution buffer may contain water, Tris-HCl, and/or TE buffer (Tris and EDTA). Any suitable elution buffer can be used in the method described herein. In some embodiments, the elution buffer is water. Elution of DNA may be maximized by allowing the elution buffer to contact the solid support for a few minutes before centrifugation, and in some embodiments, the eluting step can be repeated. Elution buffer can be prepared using routine methods in the art, such as those described in, e.g., Sambrook et al., *Molecular Cloning: A Laboratory Manual*, 4th ed., Cold Spring Harbor Press, Cold Spring Harbor, N.Y. (2012); and Ausubel et al., *Current Protocols in Molecular Biology*, John Wiley & Sons, New York (2016), or obtained from commercial sources. A suitable volume for elution buffer to be used may be determined by the concentration of DNA required for future analysis.

f) Downstream Analysis of Eluted DNA

DNA isolated in accordance with the method described herein may be used in downstream analytical methods. For example, the isolated DNA may be used as a template for polymerase chain reaction ("PCR"). The isolated DNA also may be used as a template for any variant of PCR, such as, for example, real-time or quantitative PCR (qPCR), allele-specific PCR, asymmetric PCR, colony PCR, degenerate PCR, miniprimer PCR, multiplex PCR, inverse PCR, nested PCR, touchdown PCR, ligation-mediated PCR, hot-start PCR, and the like (see, e.g., Singh et al., *Int. J. Adv. Res. Biol. Sci.*, 1(7): 65-80 (2014)). Other methods for DNA detection and analysis include, for example, Southern blot, DNA microarray, and fluorescent in situ hybridization (FISH).

Such DNA analysis methods may be used in a variety of applications, such as, for example, food, agricultural, horticultural, forensic science, and medical applications. In particular, the isolated DNA prepared according to the method described herein may be used to diagnose a large number of diseases and conditions, including, but not limited to, genetic diseases, prenatal abnormalities, and certain types of cancer.

In addition, isolated DNA can be used to detect the presence of certain infectious agents in an animal's bloodstream, as discussed above.

3. Kits

The elements and components of the method described above may be used in the form of a kit. The kit may comprise one or more containers (e.g., vials, bottles, or strips) comprising the method components, reagents needed for performing the method (e.g., lysis buffer, washing buffer(s), and elution buffer), and instructions for performing the method.

The kit may include a cartridge that includes a microfluidics module. In some embodiments, the microfluidics module may be integrated in a cartridge. The cartridge may be disposable. The cartridge may include one or more reagents useful for practicing the methods disclosed herein. The cartridge may include one or more containers holding the reagents, as one or more separate compositions, or, optionally, as admixture where the compatibility of the reagents will allow. The cartridge may also include other material(s) that may be desirable from a user standpoint, such as buffer(s), a diluent(s), a standard(s) (e.g., calibrators and controls), and/or any other material useful in sample processing, washing, or conducting any other step of the method.

Methods and kits used to isolate DNA in a sample obtained from cells in a blood sample can be adapted for use in a variety of automated and semi-automated systems, such as those commercially marketed, e.g., by Abbott Molecular (Abbott Park, Ill.) as m™Sample Preparation, RealTime™ PCR Assays, m2000 RealTime™ System, m24 RealTime™ System, mPlus, and m™View The present invention has multiple aspects, illustrated by the following non-limiting examples.

Example 1

This example demonstrates that DNA yield from blood samples is reduced using rapid clot collection tubes.

Whole blood containing circulating Hepatitis B virus was collected into rapid clot tubes (Z Serum Clot Activator® or BD RST® (which contains the coagulant thrombin)), or conventional serum tubes. Upon coagulation, the serum was extracted with lysis buffer and subjected to a quantitative PCR protocol for the detection of HBV DNA. The lower the FAM Cycle threshold (CT), the more HBV DNA was recovered from the serum.

Z-clot and RST tubes led to underquantitation of HBV (FIG. 1), as those tubes exhibited a higher FAM CT value than spiked serum, or serum collected into a conventional serum tube.

The results of this example demonstrate loss of DNA yield from blood samples processed in rapid clot collection tubes.

Example 2

This example demonstrates that certain rapid clot activators sequester DNA in rapid clot blood collection tubes, but that DNA binding to rapid clotting agents is reversible.

Figure 2:
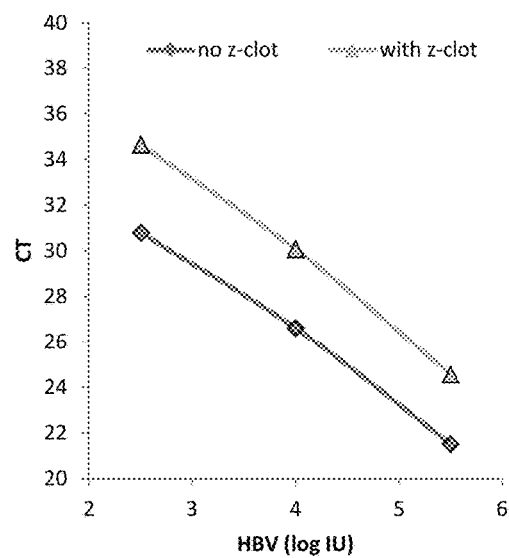
FIG. 2 contains two graphs illustrating that Z-clot rapid clot activator sequesters DNA (2A), but that DNA binding to rapid clotting activators is reversible (2B), thereby preventing analyte DNA from being available for quantitation.
Figure 2:
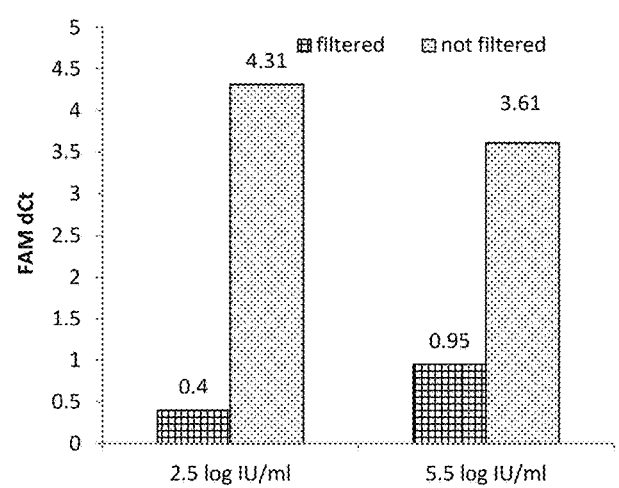

Components of Z-clot tubes that induce rapid clotting (Z-clot) were added to serum containing certain amounts of HBV virus (HBV log IU), as shown in FIG. 2A. Upon extraction, eluate from serum and serum containing clotting components were subjected to quantitative PCR. Regardless of HBV virus level used, clotting components reduced the amount of HBV DNA available for quantitation by PCR (increased CT), as shown in FIG. 2A.

DNA was collected from serum in which rapid clot agents were captured (filtered), or serum with rapid clot agents was processed without capturing rapid clot agents (not filtered). As shown in FIG. 2B, rapid clot agents sequester HBV DNA reversibly.

Example 3

This example describes a method of isolating DNA from a blood sample collected into tubes comprising a rapid clot activator which uses a lysis buffer comprising an alcohol.

Blood samples were collected into the following Zclot and SST tubes: Greiner Z-clot 456018 (5 ml), Greiner Z-clot 454243 (2.5 ml)), SST BD367989 (5 ml), and RST BD368774 (5 ml). Blood was dispensed into each tube up to the fill volume capacity of the tube. Following clotting, the blood sample was treated with proteinase K in the presence of lysis buffer and incubated for 15 minutes at 58° C. to digest proteins in the blood sample. The digested blood sample was subsequently incubated with (i) a lysis buffer (4.66M guanidine isothiocyanate, Tris pH 8, 10% Tween20) comprising varying concentrations of alcohol and (ii) magnetic microparticles for 10 minutes at 58° C. Samples were then washed with Wash 1 buffer (same as lysis buffer), followed by second and third wash steps in water (3 minutes each wash at room temperature), and dried for 3 minutes at room temperature. DNA bound to the magnetic microparticles was eluted for 10 minutes at 60° C. in water (50 µl) and used for subsequent PCR reactions to determine the presence of hepatitis B virus (HBV) DNA.

A range of alcohol concentrations in the lysis buffer was studied (from 33% to 100%). Lysis buffer containing 33% alcohol prevented loss of DNA as compared to samples treated with lysis buffer lacking alcohol and promoted preferential tethering of DNA to the magnetic microparticles, even when they were added after pK incubation at the lysis step, which may be due to direct discouragement of HBV DNA and internal control (IC) DNA binding to Z-clot microbeads. Without alcohol in the lysis buffer, HBV DNA was not sufficiently absorbed by magnetic particles when blood was collected into SST or Z-clot tubes. As a result, HBV DNA collected in rapid clot and SST tubes was severely underquantified or even undetected.

Figure 3:
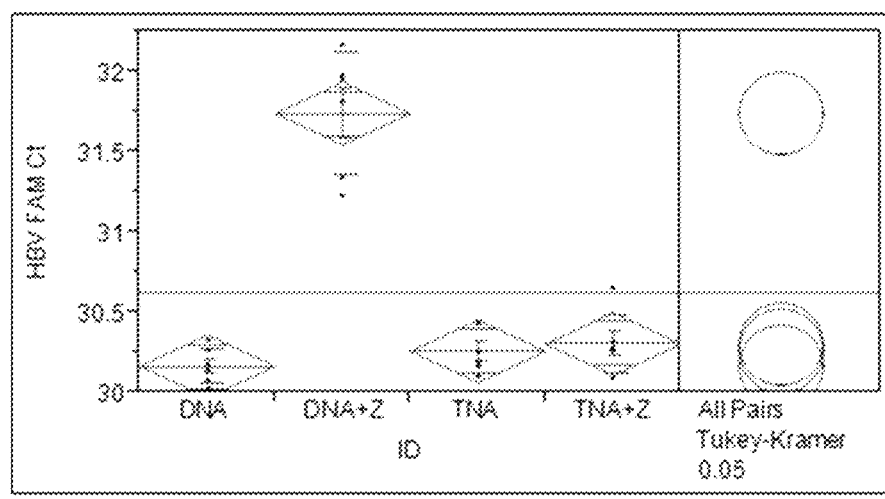
FIG. 3 is a graph illustrating the yields of Hepatitis B virus DNA isolated from blood collected in rapid clot tubes using a lysis buffer containing ethanol.

40%-65% alcohol in the lysis buffer was the optimal concentration for the lysis/wash step to allow HBV detection in samples with normal lipid levels, as shown in FIG. 3. The use of 50% ethanol (EtOH) sufficiently improved yield to achieve a limit of detection (LOD)≥95% detection of a much lower viral count. The advantage of using alcohol in the lysis buffer expanded to "stored samples" maintained for 3 days at 30° C. or 7 days at 2-8° C.

Alcohol concentrations of 65% or higher were incompatible with the described assay, and led to aggregation of silica microparticles in the presence of plasma sample bound to silica microparticles, such that the suspension could not be separated during magnet capture, resulting in microparticle carryover to the eluate and loss of detection.

The results of this example demonstrate improved DNA isolation from a blood sample collected into rapid clot activator tubes using a lysis buffer comprising 40%-65% alcohol.

Example 4

This example describes a method of isolating DNA from a blood sample having elevated lipid concentration, which is collected into tubes comprising a rapid clot activator.

Several endogenous components in blood are potential inhibitors of PCR, such as, for example, elevated lipid (hyperlipidemia). Hyperlipidemia is a prevalent condition, with an incidence of nearly half of the population (and rising). Therefore, the use of blood collection tubes that are compatible with potential endogenous interferents is essential for reliable diagnostic and prognostic applications.

Lipids in aqueous solution have a tendency to assemble into larger-order structures, such as micelles. Alcohol has been shown to increase the likelihood of micellization by decreasing the critical micelle concentration, which is the concentration above which surfactants (i.e., lipids) will form micelles. Therefore, samples with elevated lipids, such as triglycerides, are expected to have an increased concentration of micelles in the lysis wells at elevated alcohol levels.

Serum tubes and Greiner Z-clot tubes were incubated with HBV-spiked serum samples and left to sit for 20 minutes. Serum pooled by tube type and either 3 g/dL lipid or equivalent volume was then added to sample. The samples were treated with proteinase K in the presence of lysis buffer and incubated for 5 minutes at 65° C. to digest proteins in the serum sample. The digested serum sample was subsequently incubated with (i) a lysis buffer (4.66M guanidine isothiocyanate, Tris pH 8, 10% Tween20) containing different concentrations of ethanol and (ii) magnetic microparticles for 10 minutes at 65° C. Samples were then washed with Wash 1 buffer (identical to lysis buffer), followed by second and third wash steps in water (3 minutes each wash at room temperature), and dried for 3 minutes at room temperature. DNA bound to the magnetic microparticles was eluted for 4 minutes at 80° C. in water (50 µl) and used for subsequent PCR reactions to determine the presence of HBV DNA.

In high triglyceride samples, the use of lysis buffer containing high concentrations of alcohol (50% or more) resulted in silica particles being entrapped in the surfactants that adhere to the side of lysis wells and surface of plunger. Since these silica particles have bound HBV DNA and IC DNA and remain in the lysis well, this DNA was sequestered from further processing, resulting in underquantitation of analyte and control DNA. Lowering the alcohol concentration in the lysis buffer to 45% overcame this limitation in the HBV assay.

High alcohol concentrations also affect the processing of samples with high triglyceride levels. Clinical Laboratory Standards Institute (CLSI) guidelines require assays be compatible with 3.25 g/dL triglyceride in blood.

In samples with <2 g/dL triglyceride, there was less interference with both HBV and IC signals, but at 3 g/dL underquantitation of samples was observed, which was specific to alcohol addition. This interference was due to loss of microparticles which stick to lysis wells, which are therefore unable to be transferred to wash and elution wells. Since these microparticles have bound HBV and IC DNA, these samples were underquantified.

Lowering alcohol concentration to 45% reduced the loss of microbeads in lysis wells, and improved the assay's ability to handle high triglyceride samples while maintaining ability to use Z-clot tubes.

Example 5

This example describes a method of isolating DNA from a blood sample collected into tubes comprising a rapid clot activator using different alcohols in the lysis buffer.

HBV-spiked serum was pipetted into Z-clot tubes (Greiner Z-clot 455010). The samples were incubated for about 45 minutes to mimic clotting time, followed by centrifugation at 1300 g for 10 minutes to mimic blood tube centrifugation to separate serum from cells. The supernatants were collected and tested with lysis buffers containing ethanol, methanol, or propanol during extraction. Specifically, samples were treated with proteinase K in the presence of lysis buffer and incubated for 5 minutes at 65° C. to digest proteins in the serum sample. The digested serum sample was subsequently incubated with (i) a lysis buffer (4.66M guanidine isothiocyanate, Tris pH 8, 10% Tween20) containing 45% of ethanol, methanol, or propanol and (ii) magnetic microparticles for 10 minutes at 65° C. Samples were then washed with Wash 1 buffer (identical to lysis buffer), followed by second and third wash steps in water (3 minutes each wash at room temperature), and dried for 3 minutes at room temperature. DNA bound to the magnetic microparticles was eluted for 4 minutes at 80° C. in water (500 and used for subsequent PCR reactions to determine the presence of HBV DNA.

Figure 4:
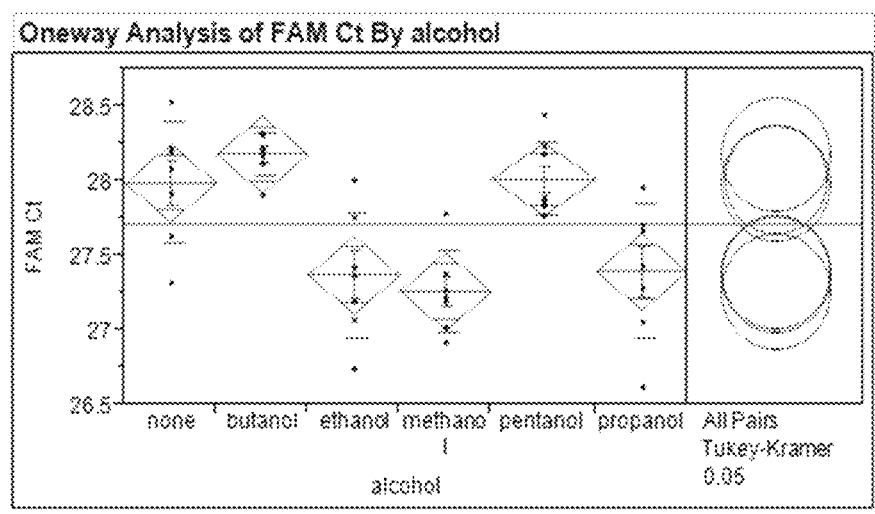
FIG. 4 is a graph illustrating the yields of Hepatitis B virus DNA isolated from blood collected in rapid clot tubes using a lysis buffer containing no alcohol (none), butanol, ethanol, methanol, pentanol, or propanol.

Lysis buffers containing ethanol, methanol, or propanol yielded similar quantitation of Hepatitis B virus DNA circulating in blood and collected in rapid clot tubes (FAM CT), as shown in FIG. 4. In contrast, lysis buffer lacking alcohol, or containing other alcohols (such as butanol or pentanol) did not support improved quantitation, as they resulted in higher FAM CT values (see FIG. 4), which indicates a delayed quantitation due to DNA loss during sample preparation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for isolating deoxyribonucleic acid (DNA) in a blood sample, the method comprising:
   (a) collecting a blood sample from a subject into tubes comprising a rapid clot activator, wherein the blood sample comprises cells, a virus, and/or bacteria;
   (b) contacting the blood sample with a lysis buffer comprising about 50% alcohol, wherein the lysis buffer lyses the cells, virus, and/or bacteria to release DNA from the cells, virus, and/or bacteria;
   (c) contacting the lysed cells, virus, and/or bacteria with a solid support which binds to the DNA;
   (d) washing the solid support bound to the DNA with a wash buffer; and
   (e) eluting the DNA from the solid support with an elution buffer, thereby isolating the DNA.

2. The method of claim 1, wherein the tubes further comprise a serum separator gel.

3. The method of claim 1, wherein the alcohol is ethanol, methanol, propanol, or combinations thereof.

4. The method of claim 1, further comprising contacting the blood sample with proteinase K before step (b).

5. The method of claim 1, further comprising contacting the blood sample with proteinase K after step (b).

6. The method of claim 1, wherein the rapid clot activator comprises silica microparticles.

7. The method of claim 1, wherein the rapid clot activator comprises thrombin.

8. The method of claim 1, wherein the solid support comprises magnetic microparticles.

9. The method of claim 1, wherein the wash buffer comprises Tris, guanidinium thiocyanate (GITC), and Tween.

10. The method of claim 1, further comprising an additional washing step with a second wash buffer before step (e).

11. The method of claim 10, wherein the second wash buffer comprises water.

12. The method of claim 1, wherein the elution buffer comprises water.

13. The method of claim 1, wherein the DNA is genomic DNA.

14. The method of claim 1, wherein the DNA is used as a template in a PCR reaction.

15. The method of claim 1, wherein the blood sample comprises cells.

16. The method of claim 15, wherein the cells are animal cells.

17. The method of claim 16, wherein the cells are human cells.

18. The method of claim 1, wherein the blood sample comprises a virus.

19. The method of claim 1, wherein the blood sample comprises bacteria.

* * * * *